(12) United States Patent
Weida et al.

(10) Patent No.: US 10,483,717 B2
(45) Date of Patent: Nov. 19, 2019

(54) LASER POWER ADJUSTMENT DURING TUNING TO COMPENSATE FOR DETECTOR RESPONSE AND VARYING BACKGROUND ABSORPTION

(71) Applicant: DAYLIGHT SOLUTIONS, INC., San Diego, CA (US)

(72) Inventors: Miles James Weida, Poway, CA (US); William Chapman, San Diego, CA (US); Bruce Coy, San Deigo, CA (US)

(73) Assignee: DAYLIGHT SOLUTIONS, INC., San Diego, CA (US)

( * ) Notice: Subject to any disclaimer, the term of this patent is extended or adjusted under 35 U.S.C. 154(b) by 0 days.

(21) Appl. No.: 16/160,822

(22) Filed: Oct. 15, 2018

(65) Prior Publication Data

US 2019/0131769 A1 May 2, 2019

Related U.S. Application Data

(60) Provisional application No. 62/580,363, filed on Nov. 1, 2017.

(51) Int. Cl.
*H01S 5/00* (2006.01)
*H01S 5/0683* (2006.01)
(Continued)

(52) U.S. Cl.
CPC ........... *H01S 5/0683* (2013.01); *G01N 21/00* (2013.01); *H01S 5/0261* (2013.01);
(Continued)

(58) Field of Classification Search
CPC ............... H01S 5/0683; H01S 5/02407; H01S 5/02469; H01S 5/06804; H01S 5/02415;
(Continued)

(56) References Cited

U.S. PATENT DOCUMENTS 6,233,045 B1 * 5/2001 Suni .................... G01C 3/08
356/28.5
6,496,525 B1 * 12/2002 Kimura .............. H01S 5/0683
372/29.01
(Continued)

OTHER PUBLICATIONS

M. J. Weida, D. Caffey, J. A. Rowlette, D. F. Amone and T. Day, "Utilizing broad gain bandwidth in quantum cascade devices", Optical Engineering 49 (11), 111120-111121-111120-111125 (2010).

*Primary Examiner* — Kinam Park
(74) *Attorney, Agent, or Firm* — Roeder & Broder LLP; Steven G. Roeder

(57) ABSTRACT

An assembly (14) for analyzing a sample (15) includes a detector assembly (18); a tunable laser assembly (10); and (iii) a laser controller (10F). The detector assembly (18) has a linear response range (232) with an upper bound (232A) and a lower bound (232B). The tunable laser assembly (10) is tunable over a tunable range, and includes a gain medium (10B) that generates an illumination beam (12) that is directed at the detector assembly (18). The laser controller (10F) dynamically adjusts a laser drive to the gain medium (10B) so that the illumination beam (12) has a substantially constant optical power at the detector assembly (18) while the tunable laser assembly (10) is tuned over at least a portion of the tunable range.

22 Claims, 10 Drawing Sheets

(51) Int. Cl.
*H01S 5/024* (2006.01)
*H01S 5/10* (2006.01)
*H01S 5/026* (2006.01)
*H01S 5/068* (2006.01)
*H01S 5/06* (2006.01)
*G01N 21/00* (2006.01)
*H01S 5/028* (2006.01)
*H01S 5/34* (2006.01)
*H01S 5/14* (2006.01)

(52) U.S. Cl.
CPC ........ *H01S 5/0264* (2013.01); *H01S 5/02407* (2013.01); *H01S 5/02453* (2013.01); *H01S 5/02469* (2013.01); *H01S 5/0612* (2013.01); *H01S 5/06804* (2013.01); *H01S 5/06808* (2013.01); *H01S 5/06817* (2013.01); *H01S 5/06837* (2013.01); *H01S 5/1092* (2013.01); *H01S 5/028* (2013.01); *H01S 5/0287* (2013.01); *H01S 5/02415* (2013.01); *H01S 5/14* (2013.01); *H01S 5/141* (2013.01); *H01S 5/3401* (2013.01); *H01S 2301/02* (2013.01)

(58) Field of Classification Search
CPC ........ H01S 5/028; H01S 5/0287; H01S 5/141; H01S 5/02453; H01S 5/3401; H01S 5/1092; H01S 5/14; H01S 5/0261; H01S 5/0264; H01S 5/0612; H01S 5/06808; H01S 5/06817; H01S 5/06837; H01S 2301/02
See application file for complete search history.

(56) References Cited

U.S. PATENT DOCUMENTS

| | | | |
|---|---|---|---|
| 7,920,608 B2* | 4/2011 | Marsland, Jr. | B82Y 20/00 372/29.011 |
| 8,189,630 B2 | 5/2012 | Marsland et al. | |
| 8,442,081 B2 | 5/2013 | Marsland et al. | |
| 8,913,637 B1 | 12/2014 | Marsland et al. | |
| 2014/0185054 A1* | 7/2014 | Atia | G01B 9/02004 356/479 |

* cited by examiner

LASER POWER ADJUSTMENT DURING TUNING TO COMPENSATE FOR DETECTOR RESPONSE AND VARYING BACKGROUND ABSORPTION

RELATED APPLICATION

The present application claims priority on U.S. Provisional Application No. 62/580,363 filed on Nov. 1, 2017, and entitled "LASER POWER ADJUSTMENT DURING TUNING TO COMPENSATE FOR DETECTOR RESPONSE AND VARYING BACKGROUND ABSORPTION." As far as permitted, the contents of U.S. Provisional Application No. 62/580,363 are incorporated herein by reference.

BACKGROUND

Semiconductor devices such as quantum cascade devices, interband cascade devices, and light-emitting diodes can be turned into tunable lasers through a variety of means. For example, a tunable laser can be an external cavity laser that includes the semiconductor device, and a tunable frequency selective element that is spaced apart from the semiconductor device. In this design, the semiconductor device is the laser gain medium, and the tunable frequency selective element is selectively tuned to adjust the center optical wavelength of an illumination beam generated by the tunable laser.

These external cavity lasers are often used in applications where it is desired to provide an illumination beam having a center optical wavelength that is varied over time over a tunable range, and then record the response of some sample as a function of the changing optical wavelength of the illumination beam. In such applications it is also often desired to tune the laser wavelength in a single sweep across the tunable range relatively quickly. This minimizes variations in the sample during data acquisition.

Unfortunately, existing semiconductor devices are not entirely satisfactory.

SUMMARY

The present invention is directed to an assembly for analyzing a sample. In one embodiment, the assembly includes (i) a detector assembly having a linear response range with an upper bound and a lower bound; (ii) a tunable laser assembly that is tunable over a tunable range, the tunable laser assembly including a gain medium that generates an illumination beam that is directed at the detector assembly; and (iii) a laser controller that dynamically adjusts a laser drive to the gain medium so that the illumination beam has a substantially constant optical power at the detector assembly while the tunable laser assembly is tuned over at least a portion of the tunable range. As used herein, the term "laser drive" shall mean and include a drive current and/or a drive voltage that is directed to the gain medium. Thus, the phrase "dynamically adjusts a laser drive" shall mean and include "dynamically adjusting a drive current" that is directed to the gain medium and/or "dynamically adjusting a drive voltage" that is directed to the gain medium.

It should be noted that each time the tunable laser assembly is tuned over a portion or the entire tunable range this event can be referred to as a scan.

With this design, the laser drive can be dynamically adjusted so that an optimum incident optical detector power is directed at the detector assembly over the tunable range, and/or the optical power directed at the sample is adjusted to compensate for background absorptions near the sample in order to ensure that the incident optical detector power directed at the detector assembly for all wavelengths in the tunable range is near an upper bound of a linear region of the detector assembly.

In alternative, non-exclusive examples, the laser controller dynamically adjusts the laser drive to the gain medium so that the illumination beam has a substantially constant optical power at the detector assembly while the tunable laser assembly is tuned over at least sixty, seventy percent, eighty percent, ninety or ninety-five percent of the tunable range.

Further, in one embodiment, the laser controller dynamically adjusts the laser drive to the gain medium so that the incident optical power of the illumination beam at the detector assembly is within approximately seventy percent of the upper bound of the linear response range for at least a seventy percent of the tunable range. In another example, the laser controller dynamically adjusts the laser drive to the gain medium so that the incident optical power of the illumination beam at the detector assembly is within approximately eighty percent of the upper bound of the linear response range for at least eighty percent of the tunable range. In yet another, non-exclusive example, the laser controller dynamically adjusts the laser drive to the gain medium as a function of wavelength so that the incident optical power of the illumination beam at the detector assembly is within approximately ninety percent of the upper bound of the linear response range for at least ninety percent of the tunable range. With these designs, the laser controller dynamically adjusts the laser drive to the gain medium so that incident optical power of the illumination beam at the detector assembly is optimized for maximum linear response and minimum noise contribution as the laser assembly is tuned over a portion or all of the tunable range.

Further, the laser controller can dynamically adjust the laser drive to the gain medium as a function of wavelength to compensate for at least one of sample absorption and background absorption around the sample.

Additionally, the assembly can include a thermal compensator positioned adjacent to and/or near the gain medium, and a temperature management system that is in thermal communication with the gain medium. In this embodiment, the laser controller can dynamically adjust a compensator drive to the thermal compensator to dynamically maintain a substantially constant thermal load on the temperature management system as the laser assembly is tuned over the tunable range.

Stated in another fashion, the laser controller can dynamically adjust the compensator drive to the thermal compensator to ensure a substantially constant net thermal load during the tuning of the laser assembly. More specifically, the laser controller can dynamically adjust the compensator drive to the thermal compensator in a wavelength varying manner to compensate for the changes in thermal load from the gain medium that result from matching the optical power to the detector assemblies or compensating for an absorbing sample or optical material background absorption.

In another embodiment, the present invention is directed to an assembly including: (i) a detector assembly; (ii) a tunable laser assembly that is tunable over a tunable range, the tunable laser assembly including a gain medium that generates an illumination beam that is directed at the detector assembly, and a thermal compensator positioned adjacent to the gain medium; and (iii) a laser controller that dynamically adjusts a laser drive current to the gain medium as a function of wavelength, and that dynamically adjusts a compensator drive current to the thermal compensator to dynamically balance the heat load to the thermal management system.

In one embodiment, the laser controller dynamically adjusts the laser drive to the gain medium so that the illumination beam has a substantially constant optical power at the detector while the tunable laser assembly is tuned over at least a portion of the tunable range.

In certain embodiments, the thermal compensator includes a heat generating element. Further, the thermal compensator can have a compensator thermal time constant that is approximately equal to a medium thermal time constant of the gain medium. For example, the laser controller can dynamically adjust the compensator drive to the heat generating element to dynamically balance the thermal load on the temperature management system.

The present invention is also directed to a method for analyzing a sample comprising: (i) providing a detector assembly having a linear response range with an upper bound and a lower bound; (ii) generating an illumination beam that is directed at the detector assembly with a gain medium of a tunable laser assembly that is tunable over a tunable range; and (iii) dynamically adjusting a laser drive to the gain medium with a laser controller so that the illumination beam has a substantially constant incident optical power at the detector assembly while the tunable laser assembly is tuned over at least a portion of the tunable range.

Additionally, the present invention is directed to a method that includes: (i) providing a detector assembly; (ii) generating an illumination beam that is directed at the detector assembly with a gain medium of a tunable laser assembly that is tunable over a tunable range; (iii) positioning a thermal compensator adjacent to the gain medium; (iv) dynamically adjusting a laser drive to the gain medium with a laser controller as a function of wavelength; and (v) dynamically adjusting a compensator drive current to the thermal compensator to dynamically balance the net thermal load to the temperature management system.

Moreover, the present invention is directed to an algorithm for both statically and dynamically determining the laser drive power as a function of wavelength to ensure that optimal compensated or non-compensated laser powers are incident on one or more detector assemblies to ensure optimal linear response.

DESCRIPTION

Figure 1:
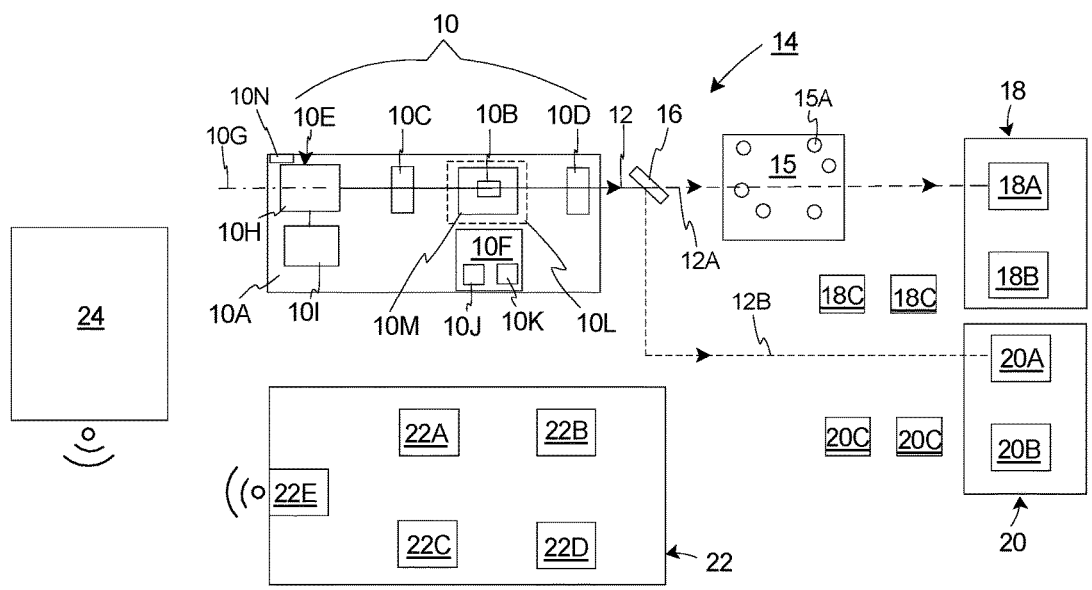
FIG. 1 is a simplified schematic illustration of a spectroscopy system that includes a laser assembly having features of the present invention.

With reference to FIG. 1, the present invention is directed to a tunable laser assembly 10 that generates an illumination beam 12 (illustrated as a solid line) having a center wavelength (wavenumber) that is varied ("tuned") over time over a tunable range. In FIG. 1, the laser assembly 10 is used with a variety of components as part of a spectroscopy system 14 (e.g. an optical spectrometer) or another type of assembly for analyzing a sample 15. In the non-exclusive embodiment illustrated in FIG. 1, the spectroscopy system 14 additionally includes a beam splitter 16, a sample detector assembly 18, a reference detector assembly 20, a spectrometer control system 22, and a remote controller 24 (i.e., a mobile device such as a phone or laptop computer). Alternatively, the spectroscopy system 14 can be designed with more or fewer components than illustrated in FIG. 1. Further, the design of each of the components of the spectroscopy system 14 can be varied.

As an overview, in certain embodiments, a laser drive current or laser drive voltage (collectively "laser drive") to the laser assembly 10 is dynamically adjusted during tuning over the tunable range so either (i) the illumination beam 12 has a substantially constant incident optical power at the sample detector assembly 18, (ii) the illumination beam 12 has a substantially constant incident optical power at the reference detector assembly 20, and/or (iii) the illumination beam 12 has a substantially constant optical power exiting the laser assembly 10. With this design, the laser drive can be dynamically adjusted so that an optimum incident optical detector power is directed at the detector assemblies 18, 20 over the tunable range, and/or the optical power directed at the sample 15 is adjusted to compensate for sample absorptions and/or background absorptions near the sample 15 in order to ensure that the incident optical detector power directed at the sample detector assembly 18 for all wavelengths in the tunable range is near an upper bound of a linear region of the sample detector assembly 18.

The type of sample 15 analyzed by the spectroscopy system 14 can vary. As non-exclusive examples, the sample 15 can be a liquid, a complex mixture of multiple liquids, or a complex mixture of liquids, dissolved chemicals, and/or one or more solids.

The tunable laser assembly 10 generates the illumination beam 12 that is used to analyze and interrogate the sample 15. Stated in another fashion, the laser assembly 10 can be tuned to different center wavelengths over time to interrogate the sample 15 at different wavelengths. In FIG. 1, the tunable laser assembly 10 is a single, external cavity, having a Littrow configuration and has the tunable range. Alternatively, the laser assembly 10 can include multiple individually tunable lasers that span a portion or all of a desired spectral range for the spectroscopy system 14. For example, when multiple lasers assemblies (not shown) are used, each laser assembly can generate a different portion of the desired spectral range, with slight overlapping of the wavelengths generated to allow for calibration of the laser assemblies and better fidelity. A description of a system that includes multiple individual laser assemblies is described in U.S. Pat. No. 9,086,375, entitled "Laser Source With A Large Spectral Range". As far as permitted, the contents of U.S. Pat. No. 9,086,375 are incorporated herein by reference. The assembly can utilize a variety of methods to rapidly switch between the target optical wavelengths. These include techniques such as rapid tuning mechanisms, galvo-controlled mirrors to switch between different laser modules, or spectral beam combining techniques of multiple laser modules and subsequent time-division multiplexing of laser illumination.

In FIG. 1, the laser assembly 10 includes (i) a laser frame 10A, (ii) a gain medium 10B (iii) a cavity optical assembly 10C, (iv) an output optical assembly 10D, (v) a tunable frequency selective element 10E, and (vi) a laser controller 10F. The design of each of these components can be varied. In alternative, non-exclusive examples, the size of the tunable (wavelength) range can be at least approximately 2, 3, 4, 5, 8, 10, 15, 18, 20 or 25 micrometers. In additional, alternative, non-exclusive examples, the size of the tunable (wavenumber) range can be at least approximately 50, 100, 200, 300, 400, 500, 1000, 2000, 3000, 4000, 4500, or 5000 cm−1 wavenumbers. However, the size of the tunable range can larger or smaller than these amounts.

In certain non-exclusive embodiments, the tunable laser assembly 10 is a tunable mid-infrared light source that directly generates and emits a substantially temporally coherent illumination beam 12 having a center wavelength that is in the mid-infrared ("MIR") range. In this example, the tunable range can be the MIR range or a portion thereof. As used herein, the term "MIR range" shall mean and include the spectral region or spectral band of between approximately five thousand to five hundred wavenumbers (5000-500 cm$^{-1}$), or approximately two and twenty micrometers (2-20 µm) in wavelength. The mid-infrared range is particularly useful to spectroscopically interrogate the sample 15 since many samples 15 are comprised of molecules or groups of molecules that have fundamental vibrational modes in the MIR range, and thus present strong, unique absorption signatures within the MIR range.

In another embodiment, the tunable range is only a portion of the MIR range. As alternative, non-exclusive examples, the tunable range can be the wavelength range of approximately 2-10 micrometers; 10-20 micrometers; 5-15 micrometers; 5-10 micrometers; 10-15 micrometers; or 15-20 micrometers. In additional, alternative non-exclusive examples, the tunable range can be the wavenumber range of approximately 500-5000 cm−1; 500-1000 cm−1; 1000-1500 cm−1; 1500-2000 cm−1; 2000-2500 cm−1; 2500-3000 cm−1; 3000-3500 cm−1; 3500-4000 cm−1; 4000-4500 cm−1; or 4500-5000 cm−1.

Still alternatively, the tunable laser assembly 10 can be designed to generate the illumination beam 12 having wavelengths that are greater than or less than the MIR range. For example, the laser assembly 10 can be designed to generate the illumination beam 12 having a center wavelength in another portion of the infrared range or in the visible or ultra-violet range.

The laser frame 10A supports one or more of the other components of the laser assembly 10 and maintains these components in alignment. In certain embodiments, the laser frame 10A can include a temperature management system 10L (illustrated as a dashed box). For example, the temperature management system 10L can include a thermoelectric cooler and/or other devices for controlling the temperature of the components of the laser assembly 10.

The gain medium 10B generates the illumination beam 12 that is directed at the sample 15 and the detector assemblies 18, 20. The design of the gain medium 10A can be varied pursuant to the teachings provided herein. In one, non-exclusive embodiment, the gain medium 10B directly emits the illumination beam 12 without any frequency conversion. As a non-exclusive example, the gain medium 10B can be a semiconductor type laser. More specifically, in certain embodiments, the gain medium 10B is a Quantum Cascade (QC) gain medium, an Interband Cascade (IC) gain medium, or a mid-infrared diode. Alternatively, another type of gain medium 10B can be utilized.

In FIG. 1, the gain medium 10B includes (i) a first facet that faces the cavity optical assembly 10C and the frequency selective element 10E, and (ii) a second facet that faces the output optical assembly 10D. In this embodiment, the gain medium 10B emits from both facets along a lasing axis 10G. In one embodiment, the first facet is coated with an anti-reflection ("AR") coating and the second facet is coated with a reflective coating. The AR coating allows light directed from the gain medium 10B at the first facet to easily exit the gain medium 10B as a beam directed at the frequency selective element 10E; and allows the beam reflected from the frequency selective element 10E to easily enter the gain medium 10B.

The illumination beam 12 exits from the second facet. The reflective coating on the second facet reflects at least some of the light that is directed at the second facet from the gain medium 10B back into the gain medium 10B. In one non-exclusive embodiment, the AR coating can have a reflectivity of less than approximately 2 percent, and the reflective coating can have a reflectivity of between approximately 2-95 percent. In this embodiment, the reflective coating acts as an output coupler (e.g., a first end) for the external cavity.

In certain embodiments, the gain medium 10B is positioned on a heat sink 10M that is in thermal communication with the temperature management system 10L. For example, the heat sink 10M can be made of material with a high thermal conductivity to more efficiently couple the gain medium 10B to the temperature management system 10L. With this design, the heat sink 10M thermally connects the gain medium 10B to the temperature control system 10L.

The cavity optical assembly 10C is positioned between the gain medium 10B and the frequency selective element 10E along the lasing axis 10G, and collimates and focuses the light that passes between these components. For example, the cavity optical assembly 10C can include a single lens or more than one lens. For example, the lens can be an aspherical lens having an optical axis that is aligned with the lasing axis 10G. In one embodiment, to achieve the desired small size and portability, the lens has a relatively small diameter. The lens can comprise materials selected from the group of Ge, ZnSe, ZnS, Si, CaF2, BaF2 or chalcogenide glass. However, other materials may also be utilized.

The output optical assembly 10D is positioned along the lasing axis 10G. In this design, the output optical assembly 10D collimates and focuses the illumination beam 12 that exits the second facet of the gain medium 10B. For example, the output optical assembly 10D can include a single lens or more than one lens that are somewhat similar in design to the lens of the cavity optical assembly 10C.

The frequency selective element 10E reflects the light back to the gain medium 10B, and is used to precisely select and adjust the lasing frequency (wavelength) of the external cavity and the center optical wavelength of the illumination beam 12. Stated in another fashion, the frequency selective element 10E is used to feed back to the gain medium 10B a relatively narrow band optical frequency which is then amplified in the gain medium 10B. In this manner, the illumination beam 12 may be tuned with the frequency selective element 10E without adjusting the gain medium 10B. Thus, with the external cavity arrangements disclosed herein, the frequency selective element 10D dictates what optical frequency (wavelength) will experience the most gain and thus dominate the optical wavelength of the illumination beam 12.

A number of alternative embodiments of the frequency selective element 10E can be utilized. In FIG. 1, the frequency selective element 10E is spaced apart from the gain medium 10B and defines a second end of the external cavity. In this embodiment, the external cavity extends from the output coupler (reflective coating) on the second facet to the frequency selective element 10E.

In one, non-exclusive embodiment, the frequency selective element 10E includes a diffraction grating 10H and a grating mover 10I (e.g. a voice coil actuator) that selectively moves (e.g., rotates) the diffraction grating 10H to selectively adjust the lasing wavelength (wavenumber) of the gain medium 10B and the center wavelength of the illumination beam 12. For example, the grating mover 10I can rapidly pivot the grating angle at a high rate (e.g. 30-1500 hertz) to adjust the center wavelength over time through the tunable range. The diffraction grating 10H can be continuously monitored with a measurement system 10N, e.g. an optical encoder, that monitors the position of the diffraction grating 10H and provides for closed loop control of the grating mover 10I. With this design, the wavelength of the illumination beam 12 can be selectively adjusted in a closed loop fashion so that the sample 15 can be interrogated at many different, precise, selectively adjustable wavelength throughout a portion or the entire, desired spectral range.

Alternatively, for example, the frequency selective element 10E can be an integrated distributed feedback grating (not shown) with electrically or thermally adjustable index of refraction, or another type of frequency selective element 10E. A discussion of the techniques for realizing the full laser tuning range from a semiconductor device can be found in M. J. Weida, D. Caffey, J. A. Rowlette, D. F. Arnone and T. Day, "Utilizing broad gain bandwidth in quantum cascade devices", Optical Engineering 49 (11), 111120-111121-111120-111125 (2010). As far as permitted, the contents of this article are incorporated herein by reference.

The laser controller 10F controls the operation of the tunable laser assembly 10. In alternative embodiments, the tunable laser assembly 10 can be controlled by the laser controller 10F so that the illumination beam 12 is either pulsed or a continuous wave (CW). For example, the laser controller 10F can include one or more processors 10J and/or one or more electronic storage devices 10K.

In FIG. 1, the laser controller 10F controls of the frequency selective element 10E to control the center wavelength of the illumination beam 12. Stated in another fashion, the laser controller 10F can control the frequency selective element 10E (e.g. via the grating mover 10I) so that the center wavelength of the illumination beam 12 is varied over time over the tunable range (e.g. the entire or a portion of the MIR range) to generate the illumination beam 12 with the center wavelength that sequentially varies over time to analyze the sample 15. For example, the laser assembly 10 can be tuned, and one or more pulses can be generated having approximately the same first center wavelength ("first target wavelength"). Subsequently, the laser assembly 10 can be tuned, and one or more pulses can be generated having approximately the same second center wavelength ("second target wavelength") that is different from the first center wavelength. Next, the laser assembly 10 can be tuned, and one or more pulses can be generated having approximately the same third center wavelength ("third target wavelength") that is different from the first and second target wavelengths. This process can be repeated to a plurality of additional target wavelengths throughout a portion or the entire tunable range. As non-exclusive examples, the number of pulses at each discrete target wavelength can be 1, 5, 10, 50, 100, 200, 500, 1000, 10,000 or more.

The number of discrete target wavelengths in the set used to analyze the sample 15 can also vary according to the sample 15. As non-exclusive examples, the number of discrete target wavelengths utilized can be approximately 1, 2, 3, 4, 5, 6, 7, 8, 9, 10, 15, 20, 25, 40, 200, 226, 400, 552 or 4000 within the tunable range.

As non-exclusive examples, the laser controller 10F can control the frequency selective element 10E so that the sweep rates across the entire tunable range is less than 1 millisecond, 10 millisecond, 100 millisecond, 1 second, 10 seconds, or 100 seconds.

Additionally, the laser controller 10F dynamically adjusts the laser drive that is directed to the gain medium 10B to control the optical power of the illumination beam 12 that is generated by the laser assembly 10. In certain embodiments, the laser controller 10F dynamically adjusts the laser drive to the gain medium 10B so that the illumination beam 12 has a substantially constant power at one or both of the detector assemblies 18, 20 while the tunable laser assembly 10 is tuned over at least a portion of the tunable range. This feature of the laser controller 10F is described in more detail below.

In one embodiment, the beam splitter 16 splits the illumination beam 12 into a sample beam 12A (illustrated with long dashed line) that is directed at the sample 15, and a reference beam 12B (illustrated with short dashed line) that is directed at the reference detector assembly 20. As a non-exclusive example, the beam splitter 16 can be a 50/50 beam splitter. Alternatively, the beam splitter 16 can be another ratio, such as 90/10; 80/20; 70/30; or 60/40.

The sample detector assembly 18 receives light from the sample 15. The sample detector assembly 18 can include (i) a sample detector 18A that is sensitive to light, and can be either a thermal detector such as bolometers or pyroelectric devices, or a photo-detector such as semiconductor detectors or photomultipliers; and (ii) a detector amplifier 18B that amplifies the signal.

The reference detector assembly 20 receives the reference beam 12B. Somewhat similarly, the reference detector assembly 20 can include (i) a reference detector 20A that is sensitive to light, and can be either a thermal detector such as bolometers or pyroelectric devices, or a photo-detector such as semiconductor detectors or photomultipliers; and (ii) a reference detector amplifier 20B that amplifies the signal.

In certain embodiments, the spectrometer control system 22 can (i) control the sample detector assembly 18 to capture one or more sample data sets 18C (only two are illustrated as boxes) at each target wavelength; and (ii) control the reference detector assemblies 18 to capture one or more reference data sets 20C (only two are illustrated as boxes) at each target wavelength. More specifically, the spectrometer control system 22 can control the detector assemblies 18, 20 to capture one or more first sample data sets, and one or more reference data sets with the sample 15 illuminated at the first target wavelength. Subsequently, the spectrometer control system 22 can control the detector assemblies 18, 20 to capture one or more second sample data sets, and one or more reference data sets with the sample 15 illuminated at the second target wavelength. This process is repeated for each target wavelength until a plurality of data sets 18C, 20C are collected across the optical frequency range of interest (e.g. the tunable range). These data sets 18C, 20C can be used to analyze the sample 15.

Figure 2:
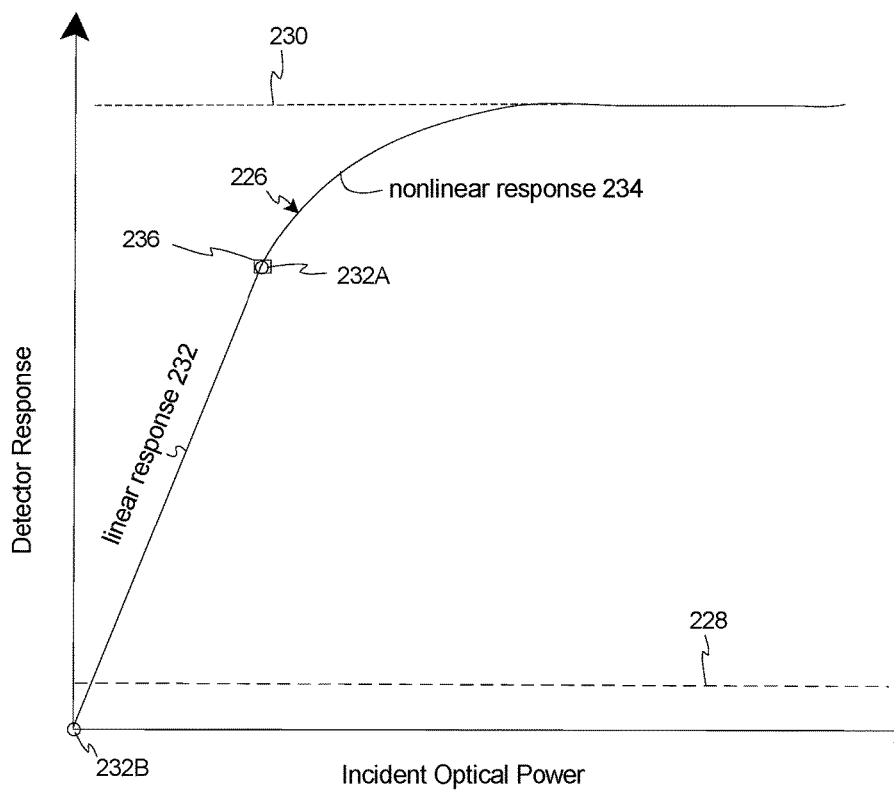
FIG. 2 is a graph that illustrates detector response versus incident optical power for a detector assembly.

Most optical detectors 18A, 20A have the following properties: (i) an intrinsic noise level, (iii) a linear response in signal to increasing optical power over a range from zero incident power to some limit, (iii) a transition from linear to non-linear response above some incident optical power, and (iv) a saturated response above some optical power. These regions of operation are illustrated in FIG. 2. More specifically, FIG. 2 is a graph that includes curve 226 that illustrates a non-exclusive example of detector response versus incident optical power for a detector (e.g. one of the detectors 18A, 20A). In FIG. 2, (i) dashed line 228 represents the intrinsic noise level for the detector, and (ii) dashed line 230 represents the saturated response level for the detector. In FIG. 2, the detector has (i) a linear response region (or range) 232 that includes a upper bound 232A (illustrated with a circle), and a lower bound 232B (illustrated with a circle), and (ii) a nonlinear response region 234 above the linear response region 234 and near the saturated response level 230.

Further, each detector 18, 20 has an optimal incident power 236 (illustrated with a small box). In a detector 18, 20 that measures absorption of a sample 15, the optimal incident power 236 of the detector 18, 20 corresponds to the highest optical power for which the detector response is still linear. Stated in another fashion, the optimal incident power 236 is at the upper bound 232A of the linear response range 232 of the detector. In this regime, the signal from the detector is at a maximum (for the linear response region 232) with respect to the intrinsic noise level 228, so detector noise effects are suppressed (minimized). If higher optical powers are used, the detector response becomes nonlinear, affecting the absorption calculation and distorting the final results.

With reference back to FIG. 1, the spectrometer control system 22 controls the various components of the spectroscopy system 14. In the non-exclusive embodiment illustrated in FIG. 1, the spectrometer control system 22 includes a system control 22A, a data acquisition system 22B, a power source 22C, a pre-processing/analysis system 22D, and a control transmitter/receiver 22E. In one embodiment, the system control 22A includes one or more processors and electronic storage devices; the data acquisition system 22B receives the data from the detector assemblies 18, 20; the power source 22C provides power to the other components; the pre-processing/analysis system 22D processes and analyzes the data from the detector assemblies 18, 20; and the control transmitter/receiver 22E transmits and receives data from the remote controller 24.

As provided above, the laser controller 10F dynamically adjusts the laser drive that is directed to the gain medium 10B to control the optical power of the illumination beam 12 that is generated by the laser assembly 10 during the sweep of the tunable range. In contrast, it is simpler to keep a constant laser drive voltage and/or laser drive current directed to the gain medium 10B during the sweep of the tunable range. This simplifies the design of the laser controller 10F, and minimizes changes in thermal load from the gain medium 10B during the sweep. However, a constant drive scheme has issues when tuning over the full range supported by the gain medium 10B. More specifically, when a constant drive scheme is directed to the gain medium 10B, the optical power of the illumination beam 12 will vary greatly across the tunable range because certain wavelengths experience greater optical power than other wavelengths. More specifically, each gain medium 10B will have a maximum output power at some wavelength, typically referred to as a gain center for the gain medium 10B. However, the efficiency for converting electrical energy into photons drops for wavelengths higher or lower than the gain center, leading to a decreasing power as the laser assembly 10 is tuned away from gain center. Therefore, with a constant drive, the laser assembly 10 outputs a range of powers throughout the sweep of the tunable range, sometimes varying by more than a factor of 10. This adversely influences the quality of the data received by the detector assemblies 18, 20.

Figure 3A:
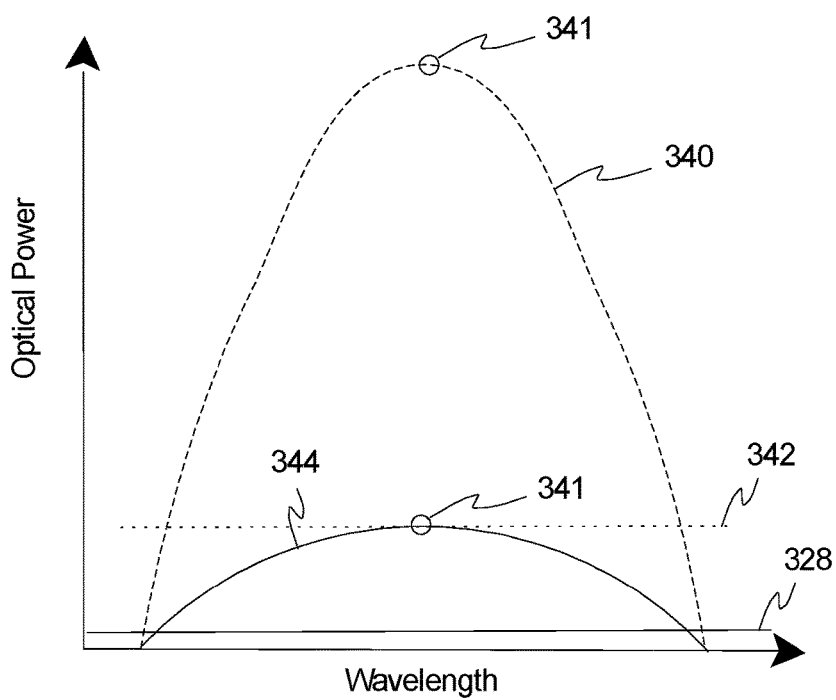
FIG. 3A is a graph that illustrates optical power generated by the laser assembly versus wavelength for a first drive profile.

As provided herein, typically, the optical powers that can be generated by the laser assembly 10 are orders of magnitude higher than the maximum incident optimal powers for the linear response for most detector assemblies 18, 20. For example, the maximum incident power for linear operation for most HgCdTe infrared photodetectors is often less than one milliwatt, while typical external cavity Quantum Cascade laser assembly 10 can generate hundreds of milliwatts of optical power. FIG. 3A is a graph that includes (i) a dashed, first curve 340 that represents the maximum possible laser output power for the laser assembly, (ii) a dotted line 342 that represents the maximum incident power for linear operation of the detector, and (iii) a solid line 328 that represents the noise level of the detector. The gain center 341 is illustrated as a circle on curve 340 and curve 344. In this example, the maximum incident power for linear operation of the detector 342 is much less than the maximum optical power output 340 generated by the laser assembly at most wavelengths.

Figure 3B:
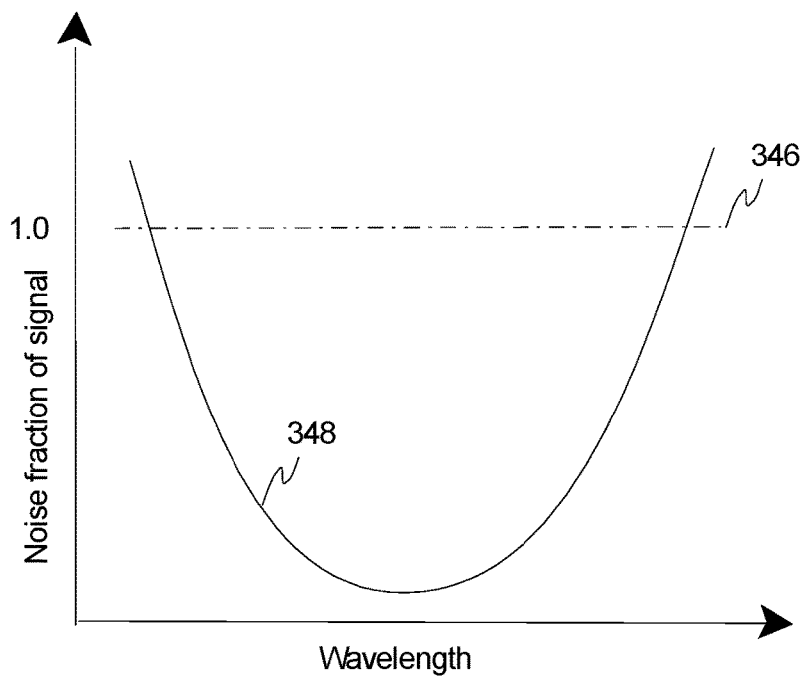
FIG. 3B is a graph that illustrates noise fraction of signal versus wavelength for the first drive profile.

In order to couple such laser assemblies 10 (illustrated in FIG. 1) to the detector assemblies 18, 20, while staying in the linear operation range of the detector assemblies 18, 20 10 (illustrated in FIG. 1), a drive paradigm (with reference to FIG. 3A) can be used. In this paradigm, the laser drive is kept constant across the tuning range (referred to as a "first drive profile") but at a lower level so that overall laser power is attenuated so that a laser power output 344 is always below the linear response range 342 of the detector assembly. Unfortunately, this has the problem that the laser power output 344 drops to either side of the gain center 341, and the relative contribution from the intrinsic noise 328 of the detector creates decreasing signal to noise away from the gain center 341. FIG. 3B is a graph that include dashed line 346 that represents the noise fraction of the signal is 1, and curve 348 that represents the relative contribution from noise. Basically, the noise level 328 (illustrated in FIG. 3A) for the detector is constant. Thus, the relative contribution from noise 348 will increase as the laser power output 344 is decreased, and the relative contribution from noise 348 will decrease as the laser power output 344 is increased.

A way around this problem of decreasing sensitivity away from gain center 341 for constant laser drive is to take advantage of the large amounts of excess optical power available from the laser assembly 10. As provided herein, instead of using a constant laser drive across the tuning range and uniformly attenuating the illumination beam as illustrated in FIG. 3A, the laser controller 10F can dynamically adjust the laser drive current and/or laser drive voltage to the gain medium 10B so that the illumination beam 12 has a substantially constant optical power at one or both of the detector assemblies 18, 20 while the tunable laser assembly 10 is tuned over at least a portion of (or the entire) tunable range.

Figure 4A:
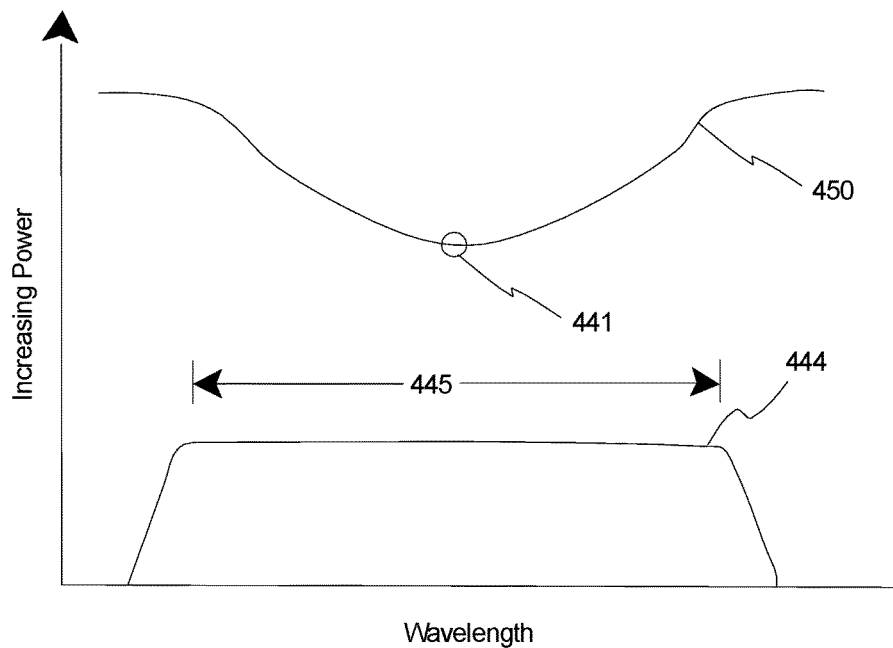
FIG. 4A is a graph that illustrates a second drive profile in which the drive current is adjusted as a function of wavelength, and the resulting modified optical power.

FIG. 4A is a graph that includes a curve 450 that illustrates a second drive profile of how the laser drive is adjusted as a function of wavelength (wavenumber) by the laser controller 10F (illustrated in FIG. 1), and a curve 444 that represents the resulting modified optical power of the illumination beam 12 (illustrated in FIG. 1) generated by the laser assembly 10 (illustrated in FIG. 1). In this example, the laser drive 450 is smallest near the gain center 441 (illustrated with a small circle) and increases as you move away from either side of the gain center 441 to achieve a substantially constant optical power 444 over the majority of the tunable range 445. With this design, in alternative, non-exclusive examples, the laser controller 10F dynamically adjusts the laser drive 450 to the gain medium 10B (illustrated in FIG. 1) as a function of wavelength so that the illumination beam 12 has a substantially constant optical power at one or both of the detector assemblies 18, 20 (illustrated in FIG. 1) while the tunable laser assembly 10 is tuned over at least sixty, seventy, seventy-five, eighty, eighty-five, ninety, ninety-five, or one hundred percent of the tunable range.

In alternative, non-exclusive embodiments, the term "substantially constant optical power" shall mean varying less than one, two, three, five, ten, fifteen, or twenty percent of the optical power.

In alternative, non-exclusive examples, the laser controller 10F dynamically adjusts the laser drive 450 to the gain medium 10B so that the incident optical power of the illumination beam 12 on one or both of the detector assemblies 18, 20 is within sixty, seventy, seventy-five, eighty, eighty-five, ninety, ninety-five, or one hundred percent of the upper bound 232A (illustrated in FIG. 2) of the linear response range 232 (illustrated in FIG. 2) for each detector assemblies 18, 20. With this design, the laser controller 10F dynamically adjusts the laser drive to the gain medium 10B so that optical power of the illumination beam 12 at each detector assemblies 18, 20 is optimized for maximum linear response and minimum noise contribution as the laser assembly 10 is tuned over a portion or all of the tunable range.

Figure 4B:
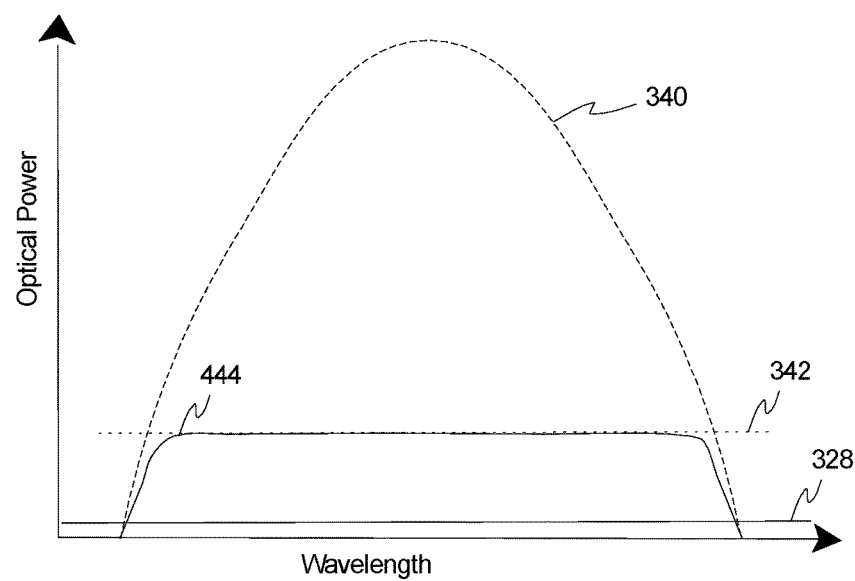
FIG. 4B is a graph that illustrates optical power generated by the laser assembly versus wavelength for the second drive profile.

Stated in yet another fashion, the laser drive 450 is varied across the tuning tunable range to keep the optical power within the linear response range 232 of the detector. In this paradigm, the laser drive 450 is dynamically adjusted (referred to as a "dynamic drive profile") as a function of wavelength across the tuning range so that incident optical power on the detector assemblies 18, 20 (one or both) is always near the upper limit 232A of the linear response range 342 of the detector assembly 18, 20. FIG. 4B is a graph that illustrates the maximum optical power 340 that can be generated by the tunable laser assembly, the linear response range 342 and the noise level 328 of the detector assembly 18, 20, and the resulting the laser power output 444 with laser assembly 10 driven with the dynamic drive profile 450 provided herein.

Figure 4C:
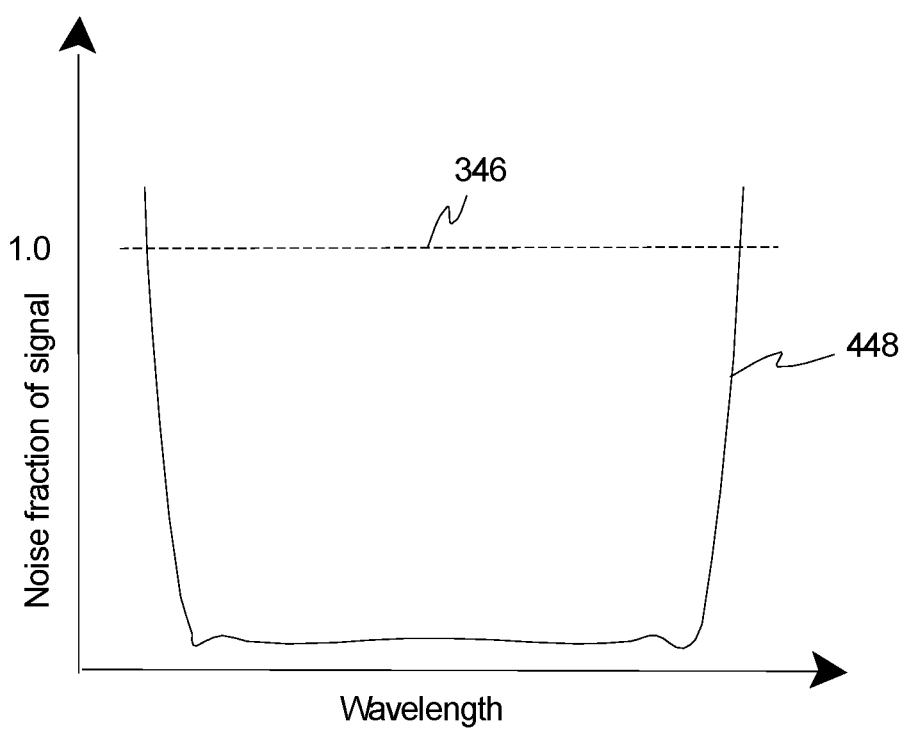
FIG. 4C is a graph that illustrates noise fraction of signal versus wavelength for the second drive profile.

FIG. 4C is a graph that includes dashed line 346 that represents when the noise fraction of the signal is one, and curve 448 that represents the relative contribution from noise when the laser assembly 10 is driven with the dynamic drive profile 450 provided herein. Basically, the noise level 328 (illustrated in FIG. 3A and 4B) for the detector is constant. Thus, the relative contribution from noise 448 will increase as the laser power output 444 is decreased, and the relative contribution from noise 448 will decrease as the laser power output 444 is increased. With this design, the relative contribution of the detector noise 448 is kept at a minimum, and is maintained substantially constant over the majority of the tunable range, and the relative contribution of the detector noise 448 is relatively small, even away from the gain center 441 (illustrated in FIG. 4A).

Thus, in this embodiment, instead of uniformly attenuating the illumination beam and using a constant drive power, the laser drive 450 is adjusted across the tuning range to level the power to the optimal amount for linear operation of the detector assembly 18, 20. This keeps the detector noise contribution fraction the same for a majority of the tuning range, and sensitivity is only decreased at the extreme edges of the tuning range where the gain diminishes to zero.

Figure 5A:
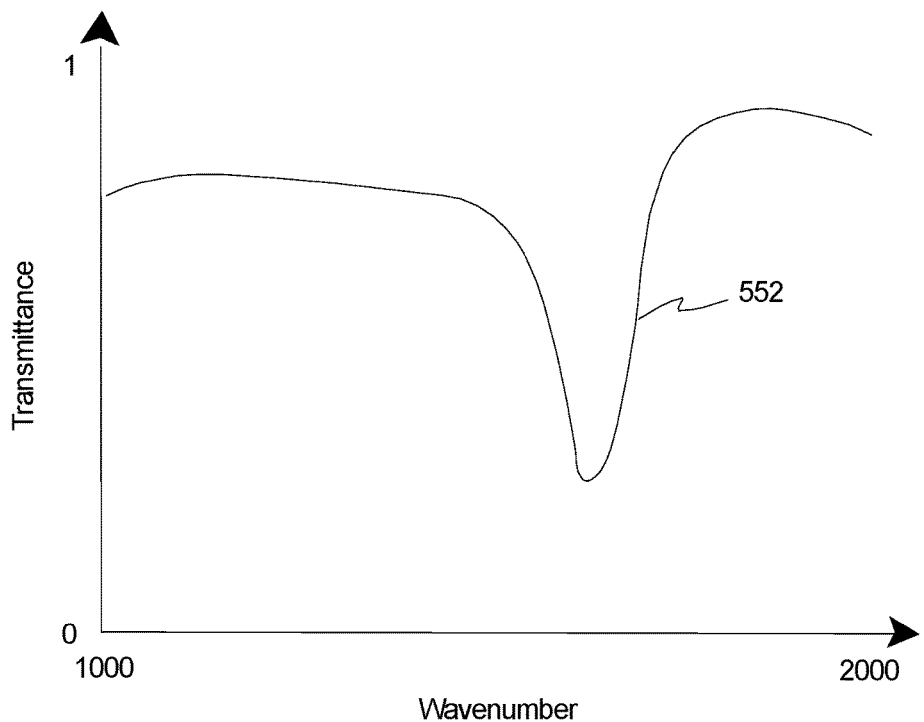
FIG. 5A is a graph that illustrates how the transmittance of the illumination beam varies as a function of wavenumber for water.

Another reason for varying the laser drive 450 to the laser assembly 10 is to compensate for light absorption of the illumination beam 15 at certain wavelengths. FIG. 5A is a graph that includes curve 552 that represents how the transmittance of the illumination beam varies as a function of wavenumber for water. Here spectroscopy of water based samples is considered. Water has a strong absorption that varies with wavelength. In this example, there is wavelength-varying background absorption, either from the sample, the background of the sample being probed (e.g., looking at solutions in water, where water has a strong wavelength absorption), or from the optical materials and coatings themselves (collectively referred to as "absorption features" and illustrated as small circles referenced as 15A in FIG. 1).

Even if a power leveling scheme such as shown FIG. 4A is used, the absorptions factors 15A will cause the incident optical power on the sample detector assembly 18 (illustrated in FIG. 1) to vary such that the relative noise contribution from the detector assembly 18 will increase, and the sensitivity thus decrease across the absorption.

Figure 5B:
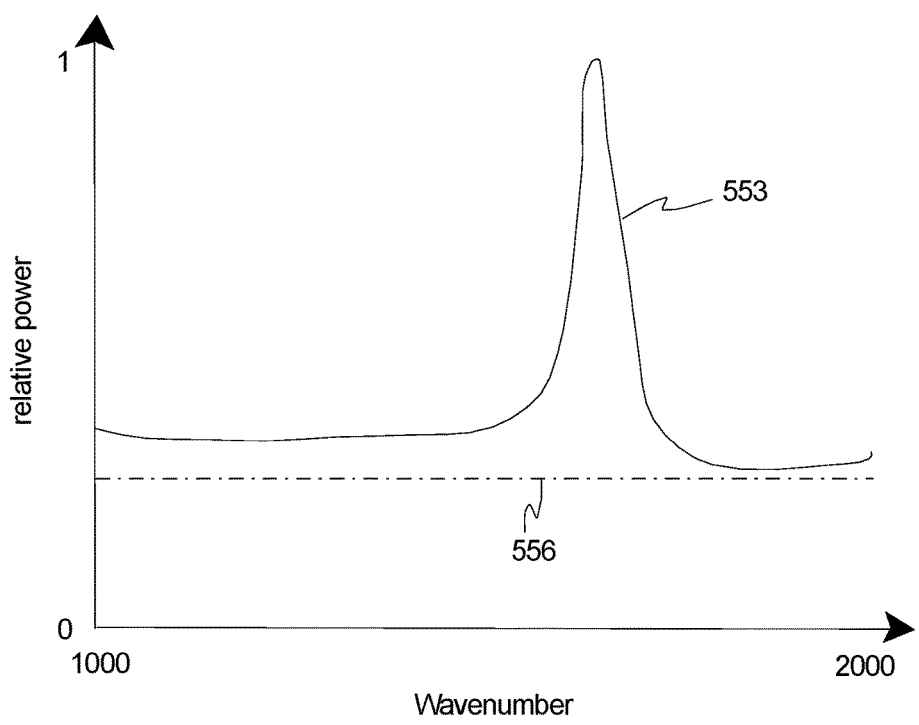
FIG. 5B is a graph that illustrates the optical power generated by the laser assembly is adjusted to compensate for the absorption and maintain the incident optical power.

With reference to FIGS. 1 and 5B, as provided herein, in certain embodiments, the laser controller 10F dynamically adjusts the laser drive that is directed to the gain medium 10B (illustrated in FIG. 1) to control the optical power of the illumination beam 12 that is generated by the laser assembly 10 during the sweep of the tunable range to compensate for absorption of the illumination beam 12.

FIG. 5B is a graph that includes curve 553 that illustrates that the optical power generated by the laser assembly 10 can be increased (by increasing the laser drive) to compensate for the absorption and maintain the incident optical power (curve 556) on the sample detector assembly 18 substantially constant (e.g. varying less than one, two, three, five, ten, fifteen, or twenty percent) while tuning the laser assembly over the tunable range. This can be achieved by varying the laser drive to the laser assembly 10 to increase the power incident on the sample at the absorption wavenumbers. With this design, the final incident optical power 556 on the detector assembly 18 is then kept at the same optimal linear operation value as the other wavelengths, and there is no reduction in sensitivity even when scanning over the varying absorption features due to the sample 15A. In this example, the laser drive is varied across the scan range to compensate for the strong absorption from water at 1650 cm−1 so that the incident optical power 556 at the detector assembly 18 stays constant and at the linear operation range maximum.

Thus, the present invention provides the laser drive can be dynamically adjusted during tuning of the laser assembly 10 to either level the optical power or compensate for background absorptions in order to ensure that the optimal linear response power level falls on the detector assemblies 18, 20 for all wavelengths in the tunable range. This can be accomplished through a calibration step, or through active control of the laser drive in a servo loop that includes a monitoring element such as a detector or some characteristic of the semiconductor device.

It should be noted that the dynamic adjustment of the laser drive causes a dynamic change in the thermal load created by the gain medium 10B on the heat sink 10M and the temperature management system 10L. As mentioned above, the time to scan or sweep across the tunable range of the laser assembly 10 can be on the millisecond to second time scale. This leads to a complication due to the changing thermal load produced by the gain medium 10B as the laser drive is varied. For example, quantum cascade devices typically only convert a few percent of the laser drive power into photons, so changing the drive current or voltage will cause a significant change in the thermal load from the device.

Figure 6A:
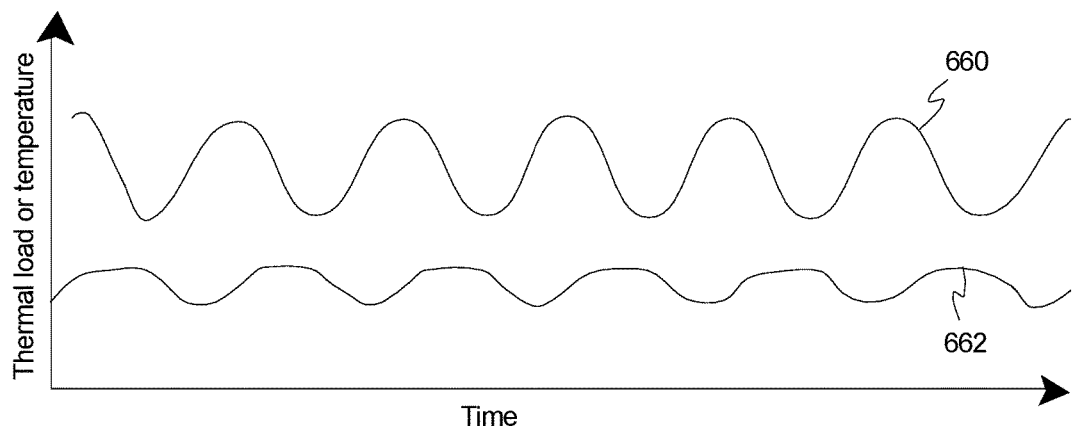
FIG. 6A is a graph that illustrates how a laser drive current/thermal load can be varied over time, and how the temperature of the laser assembly varies as a result of the variable thermal load.

FIG. 6A is a graph that includes curve 660 that illustrates how a thermal load can be varied over time as the laser drive is varied, and curve 662 that illustrates how the temperature of the gain medium varies as a result of the variable thermal load. Since most external cavity semiconductor lasers have a thermal mass that makes their thermal time constant last several seconds, it is not possible to thermally control the laser cavity on the time scale of the wavelength sweep and varying thermal load. The varying temperature is problematic because it can affect the wavelength and optical power of the laser assembly 10 (illustrated in FIG. 1). Attempting to control the frequency selective element 10E (illustrated in FIG. 1) to compensate for this oscillating temperature can cause even further oscillations.

Additionally, it should be noted that even if the laser drive to the gain medium 10B is kept constant while tuning the laser, the heat generated by the gain medium 10B will vary as the laser is being tuned. More specifically, for electrically pumped laser gain media such as laser diodes, Quantum Cascade Lasers (QCL), and Interband Cascade Lasers (ICL), the optical output power varies with the gain for a given laser drive. Stated in another fashion, when a constant drive scheme is directed to the gain medium 10B, the optical power of the illumination beam 12 will vary greatly across the tunable range because certain wavelengths experience greater optical power than other wavelengths. This is because each gain medium 10B will have a maximum output power at some wavelength, typically referred to as the gain center for the gain medium 10B as provided above. However, the efficiency for converting electrical energy into photons drops for wavelengths higher or lower than the gain center, leading to (i) a decreasing output power as the laser assembly 10 is tuned away from gain center, and (ii) an increasing thermal load created by the less efficient gain medium 10B. To adhere to the law of conservation of energy, for a constant laser drive during a laser tuning sweep, as the output power decreases, the heat created by the gain medium 10B increases.

Prior art thermal management systems cannot compensate as quickly as the wavelength (and thermal load) are changed and the result is a thermal perturbation and/or destabilization that persists after the wavelength change has occurred. This destabilization results in power and/or wavelength fluctuations that degrade the laser performance unless and until the fluctuations decay, even with a constant laser drive.

Figure 6B:
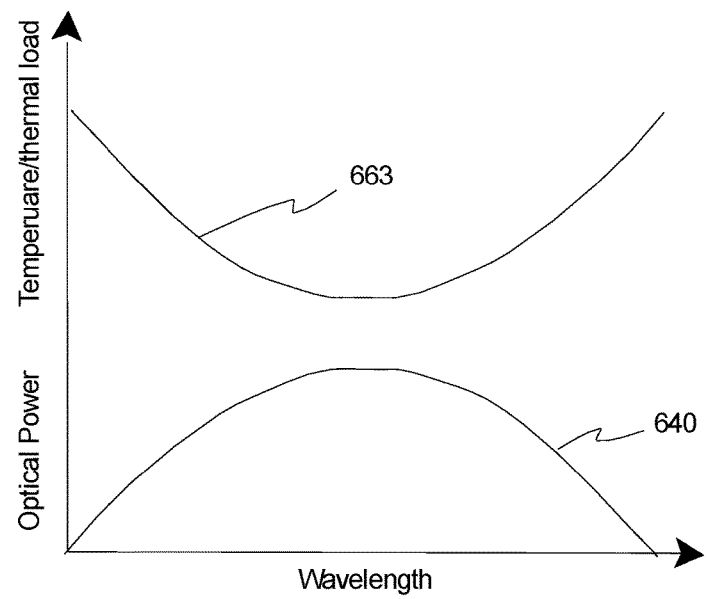
FIG. 6B is a graph that illustrates how optical power generated by the laser assembly varies versus wavelength during tuning with a constant laser drive, and how the temperature of the laser assembly varies.

FIG. 6B is a graph that includes curve 640 that illustrates how optical power generated by the laser assembly varies versus wavelength during tuning with a constant laser drive, and curve 663 that illustrates how the temperature/thermal load of the gain medium varies during tuning with a constant laser drive.

As provided herein, there are a couple of ways to compensate for these temperature/thermal load variations. The first is to let the system come to an equilibrium oscillation state. For example, for the variable laser drive, the tuning sweep rate can be held constant, and the laser drive that varies with wavelength is varied exactly the same sweep to sweep. Eventually a steady state is reached where even though the temperature is changing and hence the optical power, it is doing so consistently and can hence be ignored.

Figure 6C:
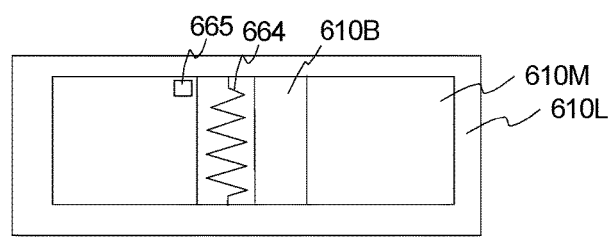
FIG. 6C is a simplified illustration of a gain medium and thermal balancer having features of the present invention.

An alternate method to compensate for the temperature variation is illustrated in FIG. 6C, which is a simplified top illustration of the temperature management system 610L (e.g. a thermoelectric cooler), the heat sink 610M, and the gain medium 610B that can be used in the laser assembly 10 of FIG. 1 or another type of laser assembly. In this example, a thermal compensator 664 is also coupled (positioned on) the heat sink 610M adjacent and near the gain medium 610B. Stated in another fashion, in this example, the thermal compensator 664 is attached proximally to the gain medium 610B.

With this design, the heat sink 610M thermally connects the gain medium 610B and the thermal compensator 664 to the thermal management system 610 so that the thermal management system 610L is in thermal communication with the gain medium 610B and the thermal compensator 664. In this embodiment, the laser controller 10F (illustrated in FIG. 1) can dynamically adjust a compensator drive current and/or compensator drive voltage (collectively referred to as a "compensator drive") to the thermal compensator 664 to dynamically maintain a substantially constant net thermal load on the temperature management system 610L as the laser assembly 10 is tuned over the tunable range.

Stated in another fashion, as the thermal load created by the gain medium 610B varies (e.g. because the laser drive is varied during tuning sweep, and/or the efficiency of the gain medium 610B varies during the tuning sweep), the laser controller 10F (illustrated in FIG. 1) directs a compensator drive (current or voltage) to the thermal compensator 664 to offset (and compensate for) the changes in thermal load created by the gain medium 610B across the tuning range.

Figure 6D:
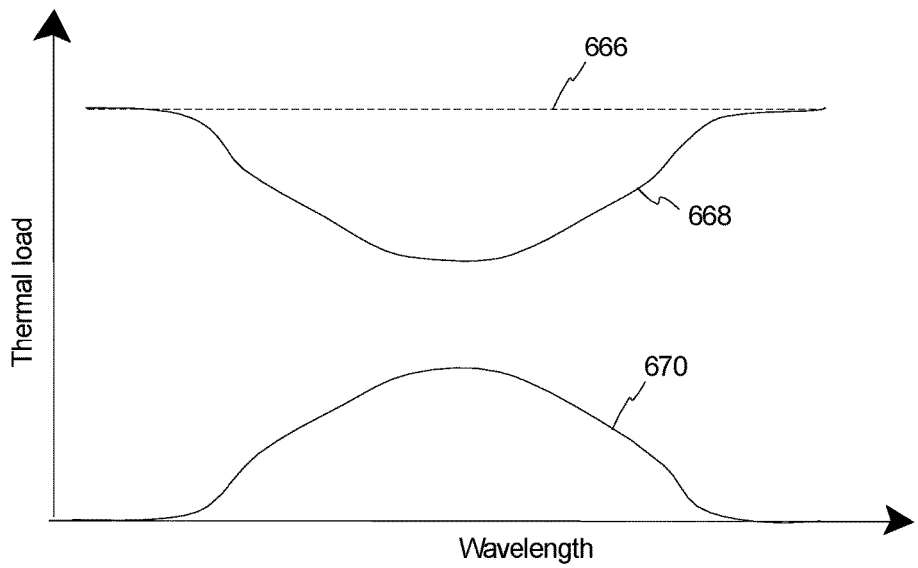
FIG. 6D is a graph that illustrates a net thermal load on a heat sink, a heat output generated by the gain medium, and a heat output generated by the thermal balancer.

FIG. 6D is a graph that includes (i) line 666 which illustrates the net thermal load on the temperature management system 610L and/or heat sink 610M as a result of the operation of the gain medium 610B (with the laser drive)

and the thermal compensator 664 (with the compensator drive); (ii) curve 668 that illustrates how the heat output generated by the laser drive to the gain medium 610B can vary over time during the tuning sweep; and (iii) curve 670 illustrates that the heat output generated by the compensator drive to the thermal compensator 664 can be controlled so that the net thermal load 666 is substantially constant. Generally speaking, during tuning, (i) as the laser drive 668 is decreased and/or the gain medium efficiency is increased, the compensator drive 670 is increased, and (ii) as the laser drive 668 is increased and/or the gain medium efficiency is decreased, the compensator drive 670 is decreased so that the net thermal load is substantially constant during tuning of the laser assembly 10 over the tunable range. As alternative examples, as used herein "substantially constant net thermal load" shall mean within ten, five, four, three, two, or one percent of no change in the thermal load. With this design, the thermal compensator 664 is used to balance out fast changes, and the temperature management system 610L is used to manage/inhibit thermal drift.

With reference to FIGS. 6C and 6D, the addition of the heat output 670 from the thermal compensator 664 is controlled with the compensator drive to compensate for the variations (e.g. reductions) in the heat output from the gain medium 610B varies (e.g. because the laser drive 668 varies and/or the efficiency varies) so that the net thermal load 666 is substantially constant during the sweep of the tunable range.

With this design, the laser controller 10F can dynamically adjust the compensator drive to the thermal compensator 664 in a wavelength varying manner to compensate for the changes in thermal load from the gain medium 610B that result in matching the optical power to the detector assemblies 18, 20 or compensating for an absorbing sample or optical material background absorption.

Further, the laser controller 10F can dynamically adjust the compensator drive to the thermal compensator 664 to dynamically maintain a sink temperature of the heat sink 610M. For example, in alternative, non-exclusive examples, the laser controller 10F can dynamically adjust the compensator drive to the thermal compensator 664 to dynamically maintain a sink temperature of the heat sink 610M so that the sink temperature varies less than five, four, three, two, one, one-half, or one-tenth percent during the tuning of the laser assembly over the tunable range. Stated in another fashion, in alternative, non-exclusive examples, the laser controller 10F can dynamically adjust the compensator drive to the thermal compensator 664 in a wavelength varying manner to dynamically maintain the sink temperature of the heat sink 610M so that the sink temperature varies less than 0.1, 0.2, 0.3, 0.4, 0.5, or 1 degrees Celsius over the tunable range of the laser.

In another example, the laser controller 10F can dynamically adjust the compensator drive to the thermal compensator 664 in a wavelength varying manner to dynamically maintain a medium temperature of the gain medium 610B. For example, in alternative, non-exclusive examples, the laser controller 10F can dynamically adjust the compensator drive current to the thermal compensator 664 to dynamically maintain the medium temperature of the gain medium 610B so that the medium temperature varies less than five, four, three, two, one, one-half, or one-tenth percent during the tuning of the laser assembly over the tunable range. Stated in another fashion, in alternative, non-exclusive embodiments, the laser controller 10F can dynamically adjust the compensator drive to the thermal compensator 664 to dynamically maintain a medium temperature of the gain medium 610B so that the variation in the medium temperature is less than 0.1, 0.2, 0.5, or 1 degrees Celsius over the tunable range of the laser.

The thermal compensator 664 can be any heat generating element (for example, a resistor, diode, or other semiconductor device). In one, non-exclusive embodiment, the thermal compensator 664 is designed to have a compensator thermal time constant that is similar (e.g. with twenty, ten, five, two, or one percent) to a medium thermal time constant of the gain medium 610B. In certain embodiments, the thermal compensator 664 is designed to allow for rapid changes in temperature for rapid response to the change temperature of the gain medium 610B.

Further, in certain embodiments, the medium thermal time constant and the thermal compensator thermal time constant are very different than a sink thermal time constant of the heat sink. Stated in another fashion, in one embodiment, the medium thermal time constant and the thermal compensator thermal time constant are much smaller that the sink thermal time constant. With this design, the compensator drive to thermal compensator 664 can be dynamically adjusted to match the fast changes to the laser drive to the gain medium 610B to dynamically maintain a substantially constant thermal load on the temperature management system 610L (and/or maintain a substantially constant gain medium temperature) as the laser assembly 10 is tuned over the tunable range.

It should be noted that the laser assembly 10 could include a temperature sensor 665 (illustrated in FIG. 6B) for closed loop temperature control of the heat sink 610M and/or the gain medium 610B with the laser controller 10F. Alternatively, because the laser drive to the gain medium 610B and efficiency of the gain medium 610B are known, the compensator drive from the laser controller 10F can be adjusted as necessary (e.g. in a feed-forward fashion) to compensate for the known changes to the laser drive command.

Still alternatively, the compensator drive to the thermal compensator 664 can be controlled by the laser controller 10F with both (i) feed-forward control (because the laser drive and efficiency of gain medium 610B are known) and (ii) feed-back control (via the temperature sensor 665 or another type of sensor). In this embodiment, the feed-back control can be used to compensate for errors in the feed-forward control during each scan (tuning of the laser assembly over the tunable range).

Additionally, or alternatively, the laser controller 10F can include iterative learning control to further refine the feed-forward command for the compensator drive during each subsequent scan. In this design, when the gain medium 610B is scanned over the tunable range, iterative learning control monitors one or more feedback parameters (e.g. temperature from the temperature sensor 665 or other sensor) and uses the information from the previous scans to improve the feed-forward, compensator drive in subsequent scans of the laser assembly. With iterative learning control, the accuracy of the feed-forward compensator drive command is improved during subsequent scans to converge on the best compensator drive to maintain the gain medium 610B at the desired temperature.

With the present design, the addition of an electrically driven thermal compensator 664 near the gain medium 610B can be used to respond to changing gain medium thermal loads on a suitably short time scale. The thermal compensator 664 may be driven to generate an amount of heat that is substantially similar to the difference of heat dissipated by the gain medium 610B over the tunable range. The thermal compensator 664 may similarly be used to compensate for changes in the laser drive. Further, the thermal compensator 664 may be driven to compensate for differences in heat dissipated by the gain medium 610B arising from generalized state changes in the laser. The thermal compensator 664 may be used as part of a feedback servo system. The thermal compensator 664 may be used as part of a feed-forward or state-based control system. The thermal compensator 664 may be combined with other elements such as the temperature management system 610L to provide improved thermal management. In one such embodiment, the thermal compensator 664 is driven in such a way that variations of the heat-load into the temperature management system 610L are reduced or minimized. In another embodiment, the thermal compensator 664 is responsive to the differential term in a PID control loop.

Figure 6E:
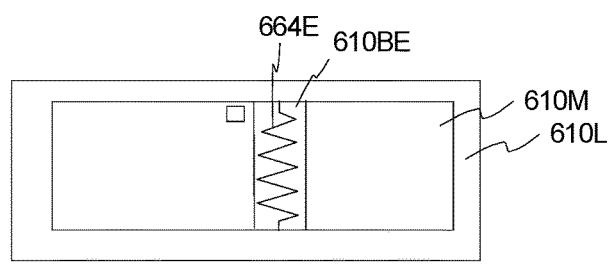
FIG. 6E is a simplified illustration of another embodiment of the gain medium and the thermal balancer.

FIG. 6E is a simplified illustration of the temperature management system 610L, the heat sink 610M, and another, non-exclusive, embodiment of the gain medium 610BE and the thermal compensator 664E. In this embodiment, the thermal compensator 664E is deposited directly onto the gain medium 610BE, e.g. by metal vapor deposition.

Figure 6F:
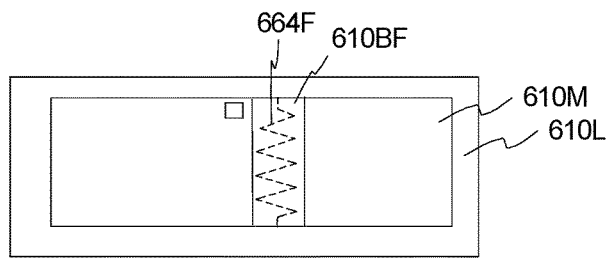
FIG. 6F is a simplified illustration of still another embodiment of the gain medium and the thermal balancer.

FIG. 6F is a simplified illustration of the temperature management system 610L, the heat sink 610M, and yet another, non-exclusive, embodiment of the gain medium 610BF and the thermal compensator 664F. In this embodiment, the thermal compensator 664F is designed into the epitaxial growth structure of the gain medium 610BF. With this design, the thermal compensator 664F is integrated directly into the gain medium 610BF.

In yet another embodiment, the tunable laser assembly 10 can be calibrated during manufacturing (i) to determine the variable, laser drive that will result in matching the optical power to the detector assemblies 18, 20 and/or compensating for an absorbing sample or optical material background absorption during the tuning of the laser assembly over the tunable range; and/or (ii) to determine the variable, compensator drive that results in the net thermal load being substantially constant during the tuning of the laser assembly over the tunable range, and/or maintaining a constant gain medium temperature.

As provided herein, two, non-exclusive procedures can be used to determine the calibration curve that dictates the change in laser drive versus wavelength. The first is a static power calibration, shown sequentially in FIG. 7. In this static mode an initial power calibration as a function of tuning wavelength is performed. The system is stepped by wavelength intervals over its tuning range and allowed to equilibrate before moving to the next wavelength. The laser power is then adjusted until a target value on the detector is observed.

Starting at block 700, the static power calibration is started. Next, at block 702, the input wavelength scan range, and the gain medium drive maximum target power at the detector is inputted. Subsequently, at block 704, the grid of wavelength steps are calculated. Next, at block 706, the laser assembly is tuned to the starting wavelength. Subsequently, at block 708, the laser drive is reduced to the minimum amount. Next, at block 710, one or both of the detector assemblies measure the incident power. Subsequently, at block 712 the measured incident power is compared to the target value of the incident power. If the measured incident power is not equal to the target incident power, at block 714, is the laser drive command at the maximum amount? In no, at block 716, the laser power is increased, and blocks 710 and 712 are repeated until the measured incident power is equal to the target incident power or the laser drive is at the maximum amount.

Once the measured detector power is at the target value 714 in block 712, or at the maximum drive in block 714, the laser drive for that wavelength is stored at block 720, and transferred to block 722 which is the static power calibration data table of laser drive versus wavelength. Subsequently, at block 724, is the wavelength at the end of range? If no, the next wavelength is selected, and the laser assembly is tuned to this wavelength. Next blocks 710, 712, 714, 716, 720, 722, 724, and 726 can be repeated until all of the wavelengths have been calibrated. When all of the wavelengths have been calibrated, the static power calibration is complete at block 728. This static calibration is then stored and used as the basis for a subsequent dynamic calibration.

Figure 7:
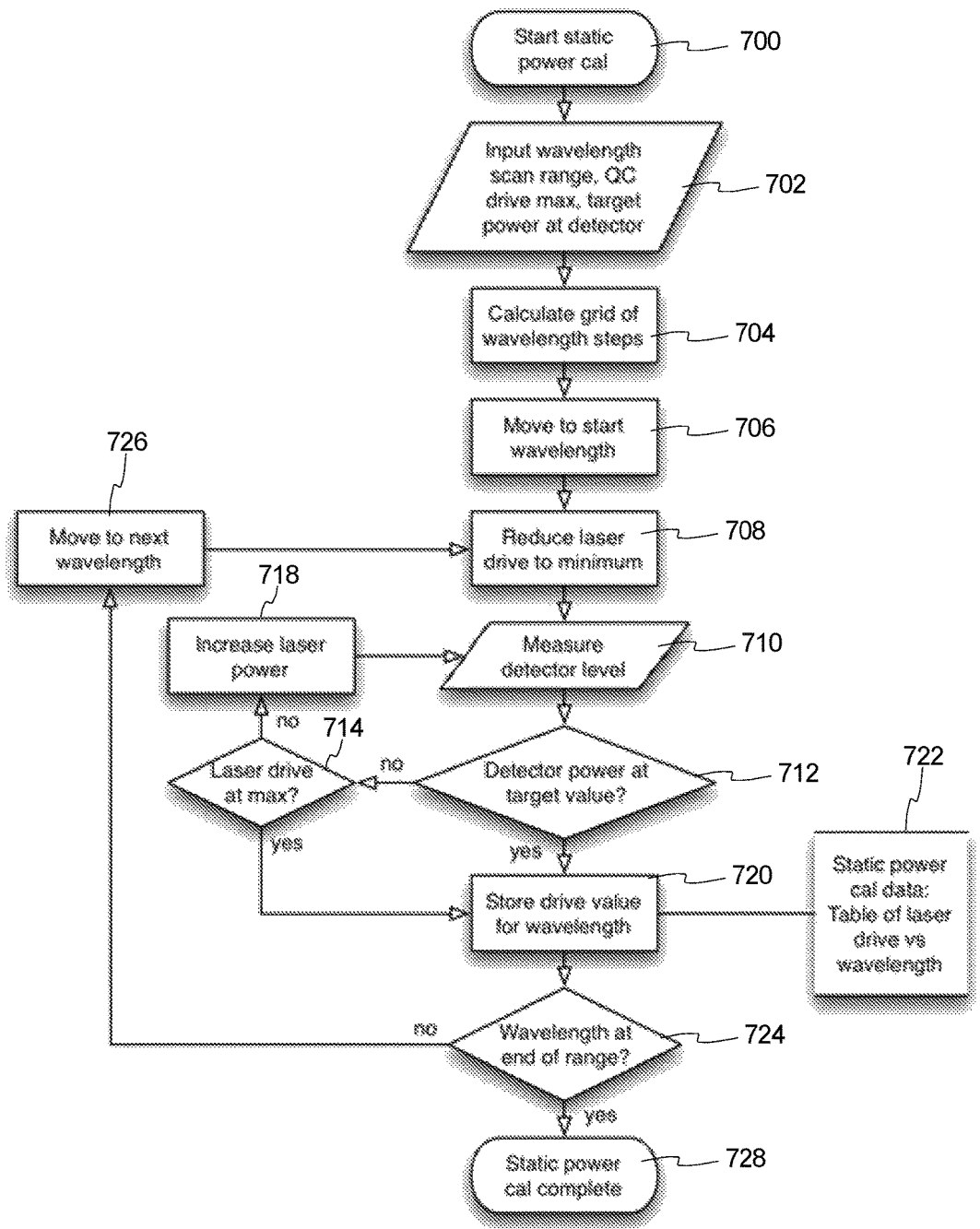
FIG. 7 is a flow chart that illustrates a procedure for static power calibration.

In practice, as the laser assembly is rapidly swept over its entire tuning range, the rate of tuning, as well as the wavelength step size and other laser drive conditions affect the ultimate power output from the laser assembly. Hence, the static power calibration illustrated in FIG. 7 is not always sufficient. Instead, a dynamic power calibration as detailed in FIGS. 8 and 9 can be carried out to provide a more accurate calibration.

Figure 8:
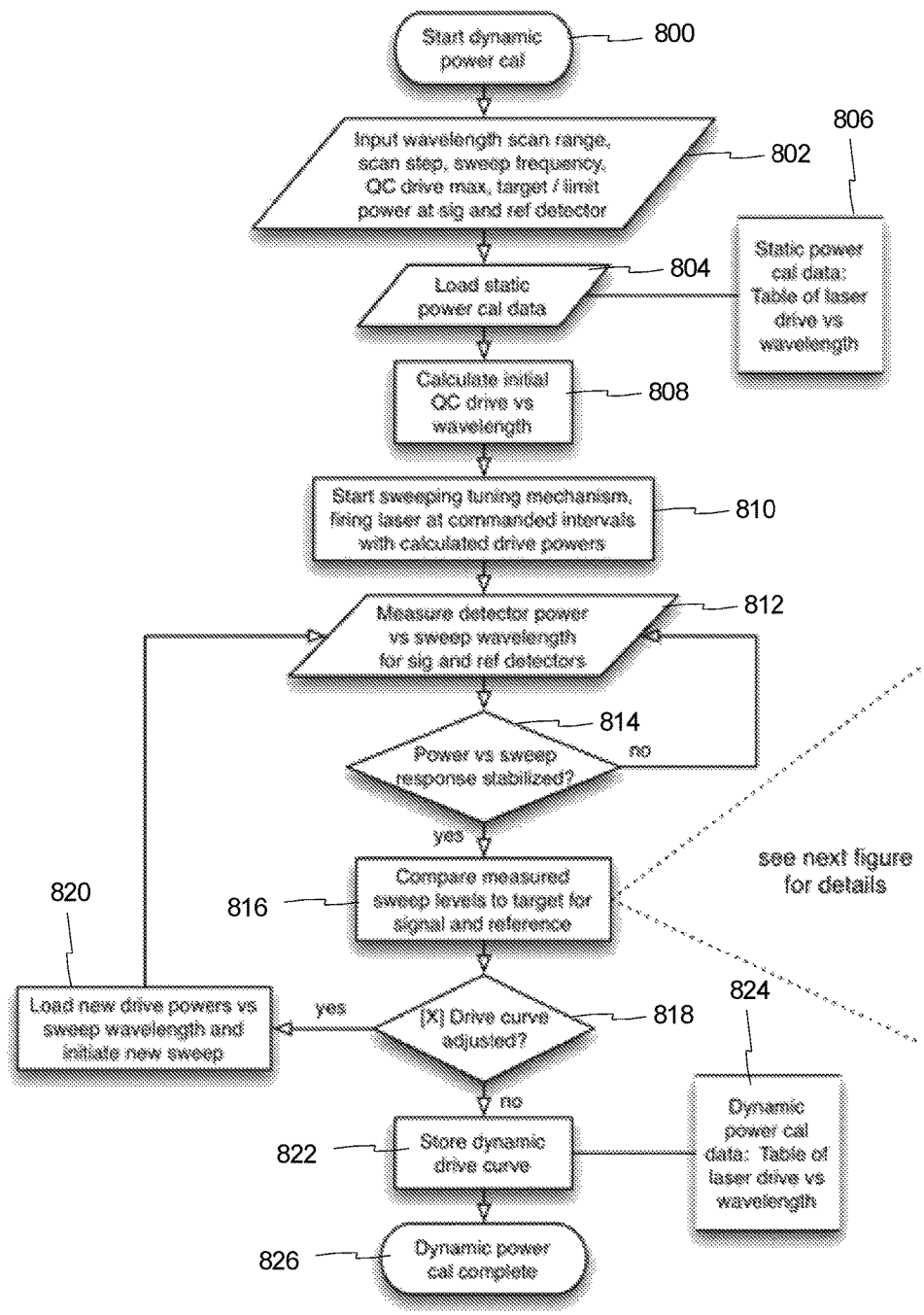
FIG. 8 is a flow chart that illustrates a procedure for dynamic power calibration.

With reference to FIG. 8, at block 800, the dynamic power calibration is started. Subsequently, at block 802, (i) the wavelength scan range, (ii) the scan step, (iii) the sweep frequency, (iv) the gain medium maximum laser drive, and (v) the target/limit incident optical power at the detector assemblies are inputted. Next, at blocks 804, 806 the static power calibration data from FIG. 7 is loaded. Subsequently, at block 808, the initial laser drive for each wavelength is calculated. Next, at block 810, the sweeping of the frequency selective element is started and the laser drive is directed to the gain medium at the commanded intervals with the calculated drive powers.

Subsequently, at block 812, the detector power is measured with the detector assemblies (signal and reference) for each wavelength in the tunable range. Next, at block 814, is the system analyzes if the power versus sweep response is stabilized? If no, block 812 is repeated until it is stabilized. If the power versus sweep response is stabilized, at block 816, the measured sweep levels to target for the detector assemblies is compared as provided in FIG. 9. Next, a block 818, the system analyzes if drive curve needs to be adjusted so that the measured sweep levels are equal to the target levels? In yes, at block 820, new drive powers versus sweep wavelength are loaded and a new sweep is initiated. Subsequently blocks 812, 814, 816 and 818 are repeated until the answer at block 818 is no. Next, the dynamic drive curve is stored at block 822 and a dynamic power calibration data, and a table of laser drive versus wavelength is created at block 824. Next, at block 826, the dynamic power calibration is complete.

Figure 9:
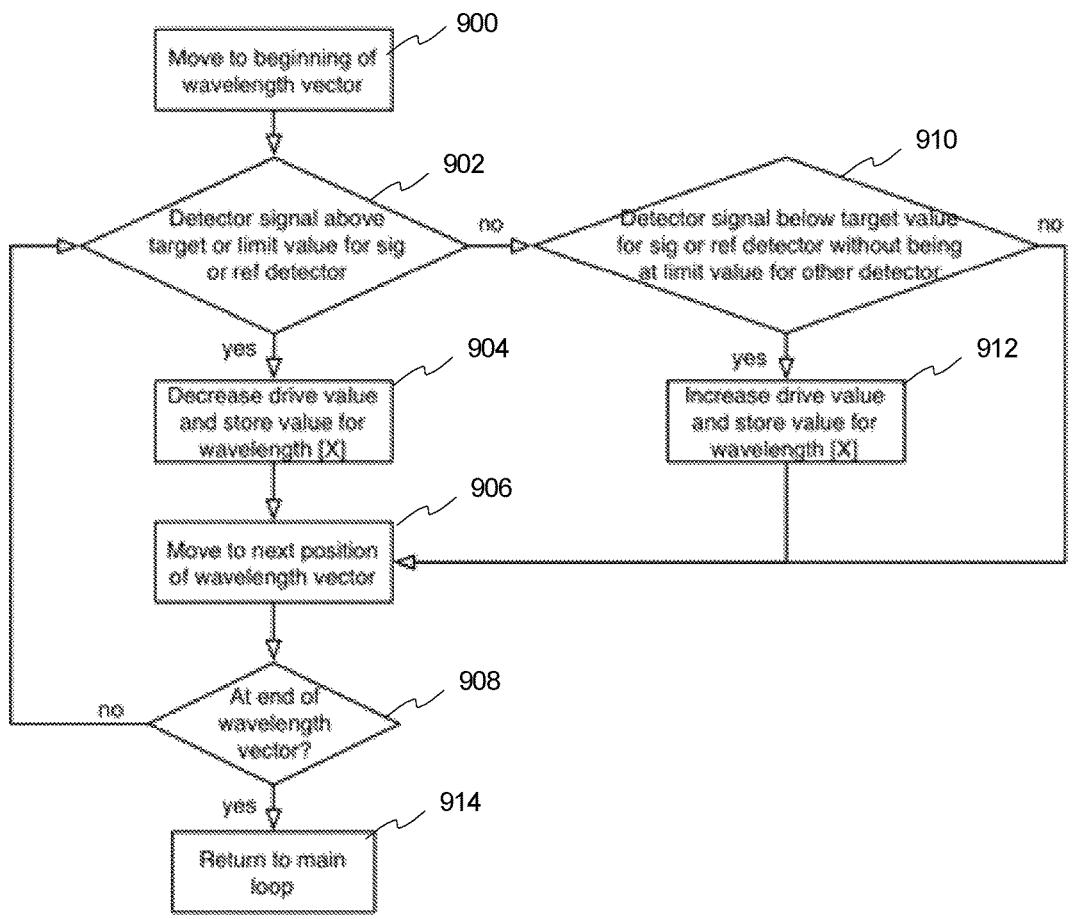
FIG. 9 is a flow chart of a detailed portion of dynamic power calibration from FIG. 8.

FIG. 9 is a flow chart that illustrates one non-exclusive example of the comparison of the measured, incident optical power during the sweep to the target incident optical power. At block 900, move to the beginning of the wavelength vector. Next, at block 902, the system analyzes if the detector signal is above the target or limit value for the detector assemblies. If yes, at block 904, the laser drive is decreased and stored for wavelength [X]. Subsequently, at block 906, the system moves to the next position (wavelength) on the wavelength vector. Next, at block 908, the system evaluates if it is at the end of the wavelength vector? If no, blocks 902, 904, 906 and 908 are repeated.

If the answer at block 902 is no, at block 910, the system evaluates if the detector signal is below the target value for the detector assemblies without being at the limit value for the other detector? If yes, at block 912, the drive value is increased and stored for that wavelength and the system proceeds to block 906. If the answer at block 910 is no, the system moves to block 906.

Subsequently, at block 914, the system returns to the flow chart in FIG. 8.

It should be noted that the final dynamic calibration is then stored and can be used by the laser controller 10F for controlling the laser drive during one or more subsequent scans of the laser assembly over the tunable range. More specifically, after the dynamic calibration of the laser assembly 10, during a subsequent scan, the laser controller 10F can direct the laser drive to the gain medium 10F using a feed-forward control scheme with the information from the calibration. With this design, the laser controller 10F can control the laser drive to ensure that the optimal laser power is incident on the signal and reference detectors, and can be used to compensate for wavelength-varying optical absorption from the sample background or optical materials.

Alternatively, the laser controller 10F can control the laser drive to the gain medium 10F using a feed-back control scheme with feedback from the reference detector assembly 20 (illustrated in FIG. 1) and/or other sensor feedback(s).

Still alternatively, the laser drive to the gain medium 10B can be controlled by the laser controller 10F with both (i) feed-forward control (using the calibration data), and (ii) feed-back control (with the reference detector assembly 20 and/or other sensor feedback). In this embodiment, the feed-back control can be used to compensate for errors in the feed-forward control during each scan.

Additionally, or alternatively, the laser controller 10F (illustrated in FIG. 1) can include iterative learning control to further refine the laser drive to the gain medium 10B (illustrated in FIG. 1) during each subsequent scan. In this design, when the gain medium 610B is scanned over the tunable range, iterative learning control monitors one or more output feedback parameters (e.g. the reference detector assembly 20, noise or another sensor), and uses the information from the previous scans to improve the feed-forward, laser drive in subsequent scans of the laser assembly. With iterative learning control, for example, the accuracy of the feed-forward laser drive command is improved during subsequent scans to converge on the best laser drive so either (i) the illumination beam 12 has a substantially constant incident optical power at the sample detector assembly 18, (ii) the illumination beam 12 has a substantially constant incident optical power at the reference detector assembly 20, and/or (iii) the illumination beam 12 has a substantially constant optical power exiting the laser assembly 10.

While a number of exemplary aspects and embodiments of the system have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. An assembly for analyzing a sample, the assembly comprising:
    a detector assembly having a linear response range with an upper bound and a lower bound;
    a tunable laser assembly that is tunable over a tunable range, the tunable laser assembly including a gain medium that generates an illumination beam that is directed at the detector assembly; and
    a laser controller that dynamically adjusts a laser drive to the gain medium so that the illumination beam has a substantially constant optical power at the detector assembly while the tunable laser assembly is tuned over at least a portion of the tunable range.

2. The assembly of claim 1 wherein the laser controller dynamically adjusts the laser drive to the gain medium so that the illumination beam has a substantially constant optical power at the detector assembly while the tunable laser assembly is tuned over at least seventy percent of the tunable range.

3. The assembly of claim 1 wherein the laser controller dynamically adjusts the laser drive to the gain medium so that the illumination beam has a substantially constant optical power at the detector assembly while the tunable laser assembly is tuned over at least eighty percent of the tunable range.

4. The assembly of claim 1 wherein the laser controller dynamically adjusts the laser drive to the gain medium so that the illumination beam has a substantially constant optical power at the detector assembly while the tunable laser assembly is tuned over at least ninety percent of the tunable range.

5. The assembly of claim 1 wherein the laser controller dynamically adjusts the laser drive to the gain medium so that optical power of the illumination beam at the detector assembly is within approximately seventy percent of the upper bound of the linear response range for at least a seventy percent of the tunable range.

6. The assembly of claim 1 wherein the laser controller dynamically adjusts the laser drive to the gain medium so that optical power of the illumination beam at the detector assembly is within approximately eighty percent of the upper bound of the linear response range for at least eighty percent of the tunable range.

7. The assembly of claim 1 wherein the laser controller dynamically adjusts the laser drive to the gain medium as a function of wavelength so that optical power of the illumination beam at the detector assembly is within approximately ninety percent of the upper bound of the linear response range for at least ninety percent of the tunable range.

8. The assembly of claim 1 wherein the laser controller dynamically adjusts the laser drive to the gain medium so that optical power of the illumination beam at the detector assembly is optimized for maximum linear response and minimum noise contribution as the laser assembly is tuned over a portion of the tunable range.

9. The assembly of claim 1 wherein the laser controller dynamically adjusts the laser drive to the gain medium as a function of wavelength to compensate for at least one of sample absorption and background absorption around the sample.

10. The assembly of claim 1 further comprising a temperature management system that is in thermal communication with the gain medium, and a thermal compensator positioned near the gain medium, wherein the laser controller dynamically adjusts a compensator drive to the thermal compensator to maintain a substantially constant thermal load on the temperature management system as the laser assembly is tuned over the tunable range.

11. The assembly of claim 10 wherein the laser controller dynamically adjusts the compensator drive command to the thermal compensator to dynamically maintain the medium temperature so that the medium temperature varies less than one degree Celsius during the tuning of the laser assembly.

12. The assembly of claim 10 further comprising a heat sink that thermally connects the gain medium and the thermal compensator to the thermal management system, wherein the laser controller dynamically adjusts the compensator drive command to the thermal compensator to dynamically maintain a sink temperature of the heat sink so that the sink temperature varies less than one degree Celsius during the tuning of the laser assembly.

13. The assembly of claim 1 further comprising a thermal compensator positioned near the gain medium, wherein the laser controller dynamically adjusts a compensator drive to the thermal compensator to ensure a substantially constant net thermal load during the tuning of the laser assembly.

14. The assembly of claim 13 wherein the laser controller dynamically adjusts the compensator drive to the thermal compensator in a wavelength varying manner to compensate for the changes in thermal load from the gain medium that result from matching the optical power to the detectors or compensating for an absorbing sample or optical material background absorption.

15. A method for analyzing a sample comprising:
providing a detector assembly having a linear response range with an upper bound and a lower bound;
generating an illumination beam that is directed at the detector assembly with a gain medium of a tunable laser assembly that is tunable over a tunable range; and
dynamically adjusting a laser drive to the gain medium with a laser controller so that the illumination beam has a substantially constant optical power at the detector assembly while the tunable laser assembly is tuned over at least a portion of the tunable range.

16. An assembly comprising:
a temperature management system;
a tunable laser assembly that is tunable over a tunable range, the tunable laser assembly including a gain medium that generates an illumination beam that is directed at the detector assembly, and a thermal compensator positioned near the gain medium, wherein the gain medium and the thermal compensator are in thermal communication with the temperature management system; and
a laser controller that dynamically adjusts a laser drive to the gain medium as a function of wavelength, and that dynamically adjusts a compensator drive to the thermal compensator to dynamically control a thermal load on the temperature management system as the laser assembly is tuned over the tunable range.

17. The assembly of claim 16 further comprising a detector assembly and wherein the laser controller dynamically adjusts the laser drive to the gain medium so that the illumination beam has a substantially constant optical power at the detector assembly while the tunable laser assembly is tuned over at least a portion of the tunable range.

18. The assembly of claim 16 wherein the thermal compensator includes a heat generating element.

19. The assembly of claim 16 wherein the thermal compensator has a compensator thermal time constant that is approximately equal to a medium thermal time constant of the gain medium.

20. The assembly of claim 16 wherein the laser controller dynamically adjusts the laser drive to the gain medium as a function of wavelength to compensate for at least one of sample absorption and background absorption around the sample.

21. The assembly of claim 16 wherein the laser controller dynamically adjusts the compensator drive to the thermal compensator to dynamically maintain the medium temperature so that the medium temperature varies less than one degree Celsius during the tuning of the laser assembly.

22. A method for analyzing a sample comprising:
generating an illumination beam that is directed at the sample with a gain medium of a tunable laser assembly that is tunable over a tunable range;
positioning a thermal compensator near the gain medium;
thermally connecting the gain medium and the thermal compensator to a temperature management system;
dynamically adjusting a laser drive to the gain medium with a laser controller as a function of wavelength; and
dynamically adjusting a compensator drive to the thermal compensator to dynamically control a thermal load on the temperature management system as the laser assembly is tuned over the tunable range.

* * * * *